United States Patent
Zink et al.

(10) Patent No.: US 11,058,552 B2
(45) Date of Patent: Jul. 13, 2021

(54) ANTERIOR LUMBAR INTERBODY FUSION CAGE AND PLATE

(71) Applicant: NVision Biomedical Technologies, LLC, San Antonio, TX (US)

(72) Inventors: Thomas Zink, San Antonio, TX (US); Frank Kuwamura, III, San Antonio, TX (US); Zeshan Hyder, Munster, IN (US)

(*) Notice: Subject to any disclaimer, the term of this patent is extended or adjusted under 35 U.S.C. 154(b) by 205 days.

(21) Appl. No.: 16/012,834

(22) Filed: Jun. 20, 2018

(65) Prior Publication Data
US 2018/0368992 A1 Dec. 27, 2018

Related U.S. Application Data

(60) Provisional application No. 62/523,060, filed on Jun. 21, 2017.

(51) Int. Cl.
```
A61F 2/44      (2006.01)
A61B 90/00     (2016.01)
A61B 90/90     (2016.01)
A61B 17/80     (2006.01)
A61F 2/30      (2006.01)
A61B 90/94     (2016.01)
```

(52) U.S. Cl.
CPC ........ *A61F 2/4465* (2013.01); *A61B 17/8042* (2013.01); *A61B 90/39* (2016.02); *A61B 90/90* (2016.02); *A61F 2/442* (2013.01); *A61B 17/8061* (2013.01); *A61B 90/94* (2016.02); *A61B 2090/035* (2016.02); *A61B 2090/3966* (2016.02); *A61F 2002/3008* (2013.01); *A61F 2002/30143* (2013.01); *A61F 2002/30507* (2013.01); *A61F 2002/30538* (2013.01); *A61F 2002/30578* (2013.01); *A61F 2002/30593* (2013.01); *A61F 2002/30787* (2013.01); *A61F 2002/30904* (2013.01); *A61F 2002/30911* (2013.01); *A61F 2250/0096* (2013.01)

(58) Field of Classification Search
CPC .......... A61F 2/44; A61F 2/442; A61F 2/4455; A61F 2/446; A61F 2/4465; A61F 2/447
See application file for complete search history.

(56) References Cited

U.S. PATENT DOCUMENTS 7,172,627 B2 * 2/2007 Fiere ..................... A61F 2/4611
                                                               623/17.11
7,621,938 B2 * 11/2009 Molz, IV .............. A61F 2/4611
                                                               606/246

(Continued)

*Primary Examiner* — Eric S Gibson
(74) *Attorney, Agent, or Firm* — Brennan, Manna & Diamond, LLC (57) ABSTRACT

A stand-alone ALIF implant that comprises a cage and a rotatable plate attached to an anterior portion of the cage by a fastener mechanism. The plate may also be integrally formed with the cage, and both are typically manufactured using additive manufacturing techniques. Support material may be added during the additive manufacturing process to lend support to the implant, and may be positioned around the fastener mechanism during manufacturing of the implant. Once formed, the support material may be dissolved away, thereby allowing the plate to rotate independently from the cage, but still remain movably attached via the fastener mechanism. The cage may further comprise webbing thereon to promote bone growth.

18 Claims, 5 Drawing Sheets

(56) References Cited

U.S. PATENT DOCUMENTS

| | | | |
|---|---|---|---|
| 8,425,576 B2* | 4/2013 | Anderson | A61B 17/8052 606/289 |
| 8,945,227 B2* | 2/2015 | Kirschman | A61F 2/447 623/17.16 |
| 9,101,321 B1* | 8/2015 | Kieser | A61B 17/7004 |
| 9,138,331 B2* | 9/2015 | Aferzon | A61F 2/442 |
| 9,186,257 B2* | 11/2015 | Geisler | A61F 2/447 |
| 9,271,836 B2* | 3/2016 | Pavento | A61F 2/4455 |
| 9,364,342 B2* | 6/2016 | Walkenhorst | A61B 17/7059 |
| 9,370,435 B2* | 6/2016 | Walkenhorst | A61F 2/4465 |
| 9,424,503 B2* | 8/2016 | Kieser | G06K 19/06046 |
| 9,427,330 B2* | 8/2016 | Petersheim | A61F 2/447 |
| 9,662,225 B2* | 5/2017 | Pavento | A61B 17/7059 |
| 9,668,877 B2* | 6/2017 | Pavento | A61F 2/442 |
| 9,872,781 B2* | 1/2018 | Pavento | A61F 2/30744 |
| 10,085,847 B2* | 10/2018 | Walkenhorst | A61F 2/4465 |
| 10,342,664 B2* | 7/2019 | Kieser | A61B 6/037 |
| 2005/0159813 A1* | 7/2005 | Molz, IV | A61F 2/4611 623/17.11 |
| 2008/0161925 A1* | 7/2008 | Brittan | A61F 2/4465 623/17.16 |
| 2008/0294262 A1* | 11/2008 | Levieux | A61F 2/447 623/17.16 |
| 2008/0300634 A1* | 12/2008 | Gray | A61B 17/7059 606/280 |
| 2009/0012529 A1* | 1/2009 | Blain | A61B 17/808 606/99 |
| 2009/0030520 A1* | 1/2009 | Biedermann | A61F 2/4455 623/17.16 |
| 2009/0326580 A1* | 12/2009 | Anderson | A61B 17/8894 606/246 |
| 2011/0230969 A1* | 9/2011 | Biedermann | A61B 17/8047 623/17.16 |
| 2012/0209385 A1* | 8/2012 | Aferzon | A61B 17/1671 623/17.16 |
| 2012/0316649 A1* | 12/2012 | Johnston | A61F 2/447 623/17.16 |
| 2013/0218276 A1* | 8/2013 | Fiechter | A61F 2/4455 623/17.16 |
| 2013/0238095 A1* | 9/2013 | Pavento | A61B 17/7059 623/17.16 |
| 2017/0020685 A1* | 1/2017 | Geisler | A61F 2/442 |
| 2017/0095335 A1* | 4/2017 | Kieser | A61F 2/30 |
| 2017/0333205 A1* | 11/2017 | Joly | A61F 2/4455 |
| 2018/0368992 A1* | 12/2018 | Zink | A61B 17/8042 |
| 2019/0343645 A1* | 11/2019 | Miccio | A61F 2/30771 |

* cited by examiner

FIG. 5

ANTERIOR LUMBAR INTERBODY FUSION CAGE AND PLATE

CROSS-REFERENCE TO RELATED APPLICATION

This application incorporates by reference all of the following: (i) U.S. Provisional Patent Application No. 61/938,475, filed Feb. 11, 2014; (ii) U.S. patent application Ser. Nos. 14/302,133, 14/302,171 (now U.S. Pat. No. 9,101,321) and Ser. No. 14/302,197, all filed Jun. 11, 2014; (iii) U.S. patent application Ser. No. 14/456,665, filed Aug. 11, 2014; (iv) U.S. Provisional Patent Application No. 62/035,875, filed Aug. 11, 2014; (v) U.S. patent application Ser. No. 14/823,234, filed Aug. 11, 2015 (now U.S. Pat. No. 9,424,503); (vi) U.S. patent application Ser. No. 14/822,613, filed Aug. 10, 2015 (now U.S. Pat. No. 9,414,891); (vi) U.S. Provisional Patent Application No. 62/204,233, filed Aug. 12, 2015; (vii) U.S. patent application Ser. No. 15/235,914, filed Aug. 12, 2016; (vii) U.S. Provisional Patent Application No. 62/419,341, filed Nov. 8, 2016; (viii) U.S. patent application Ser. No. 15/806,482, filed Nov. 8, 2017; (ix) U.S. patent application Ser. No. 15/805,317, filed Nov. 7, 2017; and (x) Provisional Patent Application Ser. No. 62/523,090 filed on Jun. 21, 2017.

This application claims priority from U.S. Provisional Patent Application Ser. No. 62/523,060 filed on Jun. 21, 2017.

FIELD OF THE INVENTION

The present invention relates to a vertebral implant, and more particularly to an additively manufactured anterior lumbar interbody fusion (ALIF) cage with an integral plate on the anterior section, a carrier and reading system therefor, and methods of identifying and structurally encoding implants, and systems for identifying and encoding implanted devices.

BACKGROUND

A number of medical conditions such as compression of spinal cord nerve roots, degenerative disc disease, tumor, and trauma can cause severe back pain. Intervertebral fusion is one surgical method of alleviating back pain. In an intervertebral fusion procedure, two adjacent vertebral bodies are fused together by removing the affected intervertebral disc and inserting an implant that would allow for bone to grow between the two vertebral bodies to bridge the gap left by the disc removal. Another surgical method of relieving back pain is by corpectomy. In a corpectomy procedure, a diseased or damaged vertebral body along with the adjoining intervertebral discs are removed and replaced by a spinal implant that would allow for bone to grow between the closest two vertebral bodies to bridge the gap left by the spinal tissue removal.

A number of different implant materials and implant designs have been used for interbody fusion and for vertebral body replacement with varying degrees of success. Current implant materials used include metals, radiolucent materials including plastics, elastic and polymeric materials, ceramic, and allografts. Current implant designs vary from threaded cylindrical implants to rectangular cages with teeth-like protrusions.

The intervertebral fusion cage is another tool that a spine surgeon will use in helping to treat various lower back problems. The fusion cage is a device which is inserted by the surgeon between two vertebra of a patient to relieve stresses and other causes of back pain and discomfort. Additionally, for patients that require fusion surgery to treat ailments such as degenerative disc disease, deformity and instability, an anterior lumbar interbody fusion (ALIF) cage has been shown to be effective for several reasons including, without limitation: wide surface area enabling high fusion rates; successful correction of deformity; restoration of disc height; and avoidance of neurological elements. The ALIF cage device may act as a stand-alone device to promote fusion and maintain disc height without the need for posterior surgery and instrumentation of the spine, but it may also work in conjunction with surgery and instrumentation in some cases. By way of background, an ALIF is similar to a posterior lumbar interbody fusion or PLIF, except that in the ALIF, the disc space is fused by approaching the spine through the abdomen instead of through the lower back. In the ALIF approach, a three-inch to five-inch incision is made on the left side of the abdomen and the abdominal muscles are retracted to the side to permit access to the spine area.

One issue associated with prior art ALIF cages is the tendency for the fasteners used to attached the cage to the patient's bone becoming loose, unsecured or separating from said cage, which can result in the cage being unintentionally repositioned, or the patient suffering injury.

Consequently, there is a long felt need in the art for a uniquely structured ALIF cage and rotatable plate that may be additively manufactured, integrally formed and structurally encoded. There is also a long felt need in the art for a ALIF implant that prevents the fasteners that are used to attach the implant to the patient's bone from becoming unsecured. Finally, there is a long felt need in the art for an ALIF cage/plate combination implant that is relatively easy to install in a patient, and from which secured data can be non-invasively read via a plurality of different medical imaging modalities.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

In one embodiment, the present invention includes a stand-alone ALIF implant that comprises a cage, and a plate positioned along an anterior portion of the cage and rotatable about an axis substantially perpendicular to an outboard face of the anterior portion of the cage. In addition to the anterior portion, the cage preferably comprises a top, a bottom, a posterior portion, a lateral continuous opening and a vertical continuous opening, and the plate preferably comprises a body portion and at least one opening therein. Further, the cage comprises structurally encoded data, for example, in the form of a vertical rod or other structurally encoded member.

In a preferred embodiment of the present invention, the plate is an integral part of the cage, and both are manufactured using additive manufacturing (AM) techniques. Typically, the implant is manufactured from titanium, specifically Ti 6 Al 4 V-ELI, though other suitable materials can also be used without affecting the overall concept of the present invention.

The cage and the plate are grown together as one integral component, such that the length of the plate and the height of the cage (as measured from top to bottom) are proportional to each other, and thus there is no need for a range of separate sizes in cages and plates as would typically be required. In one embodiment, the cage would be manufactured with webbing or other honey-combed like structure on its outboard of inboard surfaces to promote bone growth (or osteo-integration) within the implant.

In a further preferred embodiment of the present invention, the implant comprises a fastening mechanism comprised of a post and a flange for further securing the plate to the cage, and a support material. The support material is preferably water soluble and is added during the additive manufacturing process to lend support to the implant. More specifically, the support material may be positioned around the post during the manufacture of the implant, and holds the plate in place on the anterior portion of the cage as both components are manufactured. Once manufactured, the support material may be dissolved away, thereby allowing the two components to rotate independently from one another, but still remain movably attached via the flange.

In one embodiment, after insertion of the implant, screws or other fasteners can be inserted through the cage and into a patient's bone. After the insertion of said cage fasteners, the plate may be rotated to prevent the cage fasteners from backing out or otherwise becoming unsecured, and additional screws can be placed in openings in said plate and attached to the patient's bone to prevent the plate from further rotating and to further secure the ALIF implant to a patient's bone structure. In this manner, four or more fasteners or screws can be used to secure the ALIF implant of the present invention to a patient.

In another embodiment, the implant of the present invention further comprises a structurally encoded member, notches, or other radiopaque inclusions that interrupt an otherwise uniform surface. For example, the structurally encoded member may be in the form of a vertical rod that can be coded to match the encoded markers that may be pressed into the implant in accordance with inventions disclosed in the incorporated references. Such encoding may be accomplished for instance through the use of eclipsing patterns of marks or notches in other planes within the ALIF implant cage, to reveal a pattern upon elucidation through reading illumination or through illumination-aided visual inspection or optical inspection, as described herein.

The displayed pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices and a user interface comprising means for displaying information associated with the indicia based on the plurality of records. The encoded pattern may in turn be related to a unique numerical identifier corresponding to the associated manufacturer, serial number, installation data, patient, surgeon, or surgical procedure information that may be located in an external healthcare facility or other database.

The reading illumination may be that of any appropriate imaging modality such as those selected from the group consisting of visible light, UV light, x-ray, fluoroscopy, computed tomography, electromagnetic radiation, ultrasound, magnetic resonance imaging, positron emission tomography and neutron imaging, depending upon the nature and thickness of the implant body and the constituent adjacent first and second encoded regions and constituent series of shaped inclusions.

The implants of the present invention and the methods relating to same may further incorporate the structurally encoded pin and the applicable methods relating to the same as described in U.S. patent application Ser. No. 15/806,482, filed on Nov. 8, 2017 and entitled Elongate Implant Containing a Structurally Encoded Pin, Carrier and Reading System Therefor. Accordingly, the implants of the present invention may be directly encoded or further comprise a structurally encoded component such as a pin. Further embodiments may also include the use of embedded chips, etc. in the implant.

Accordingly, implants of the present invention may have encoded therein some information through the use of the encoded inclusion patterns of the present invention, while other information may be encoded through use of the structurally encoded pins described in the referenced application. Likewise, by combining aspects of both inventions one can use the two (or more) methods together for similar information (either for redundancy or using different methods for reading the information), different information, or some combination of the same or different information, as well as further through the use of embedded chips, etc. for other information within such an encoding scheme.

The present invention may also be applied to other industries, thereby allowing the operator to track anything in any industry with an eclipsing encoded region as described herein and a source of reading illumination, such as x-rays or the like. For example, it will be appreciated that the present invention may also be applied to other fields for the inventory management of articles in any industry, such as in the case of articles that may include parts used in manufacturing, such as in the case of automobiles, firearms, jewelry, etc., as well as parts therefor.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

While the specification concludes with claims particularly pointing out and distinctly claiming the present invention, it is believed that the present invention will be better understood from the following description in conjunction with the accompanying FIGS., in which like reference numerals identify like elements, and wherein:

DETAILED DESCRIPTION

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

Generally stated, the present invention relates to a uniquely structured ALIF cage and rotatable plate that may be additively manufactured, integrally formed and structurally encoded. Further, the ALIF cage/plate combination implant of the present invention is relatively easy to install in a patient, and contains structurally encoded information that may be read post-operatively and non-invasively by a number of different medical imaging modalities.

Figure 1:
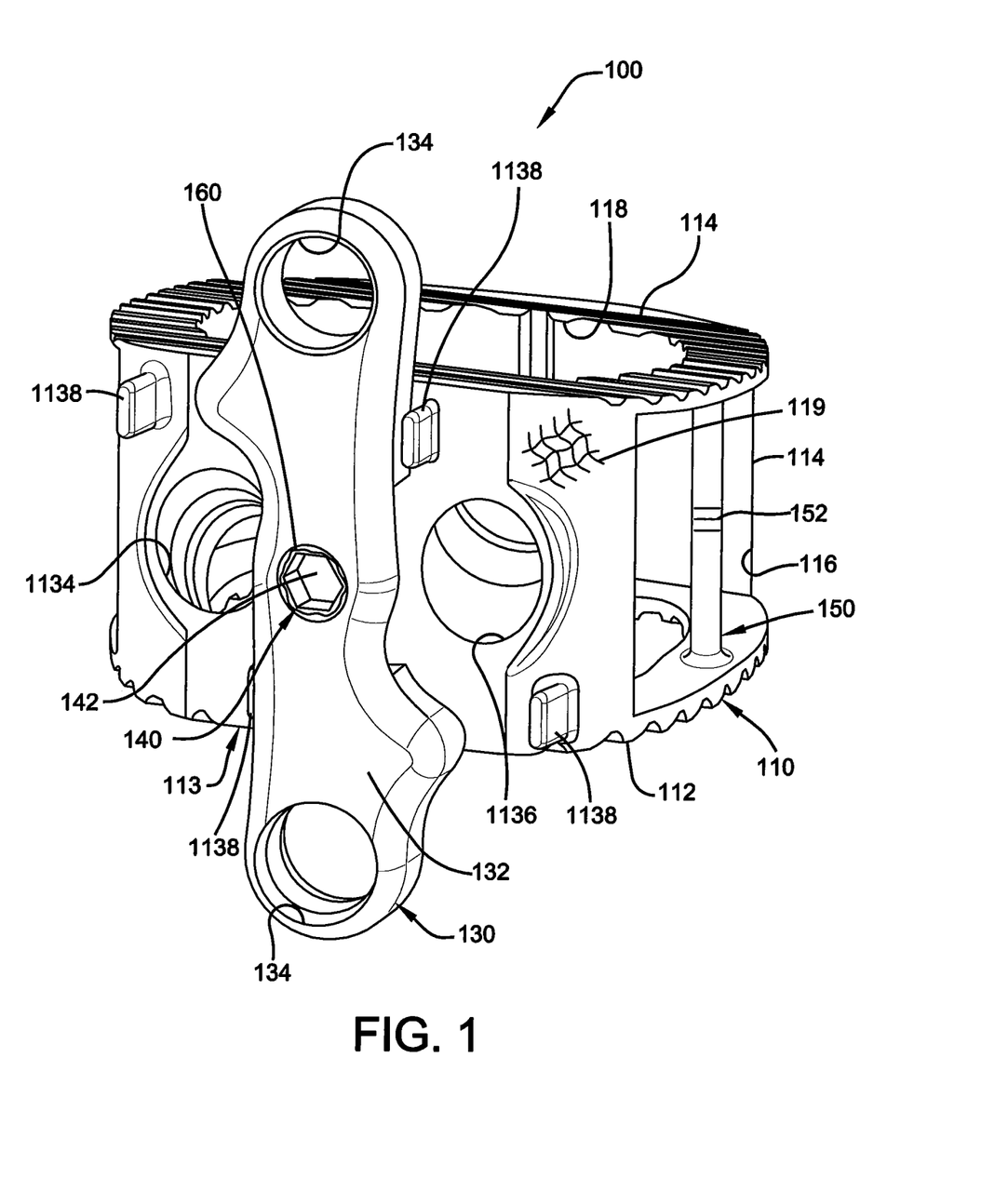
FIG. 1 illustrates a perspective view of one embodiment of the vertebral implant of the present invention in accordance with the disclosed architecture.

Referring initially to the drawings, FIG. 1 illustrates a perspective view of one embodiment of a vertebral implant 100 of the present invention. Anterior lumbar interbody fusion implant 100 is preferably comprised of a cage 110, a plate 130, a fastener system 140 for rotatably securing the plate 130 to the cage 110, and at least one structurally encoded member 150.

Figure 2:
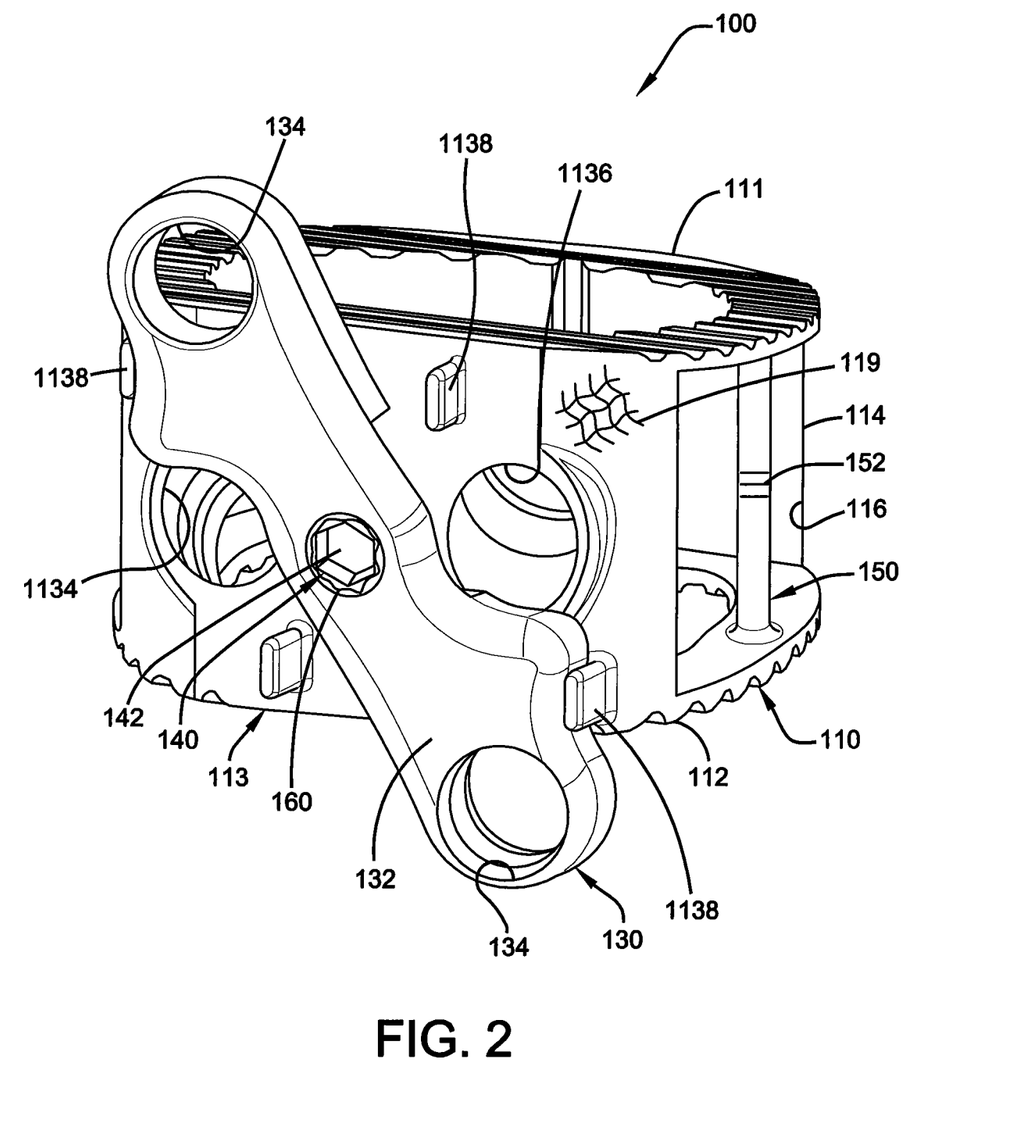
FIG. 2 illustrates a perspective view of the vertebral implant of FIG. 1 with the plate rotated in accordance with the disclosed architecture.
Figure 3:
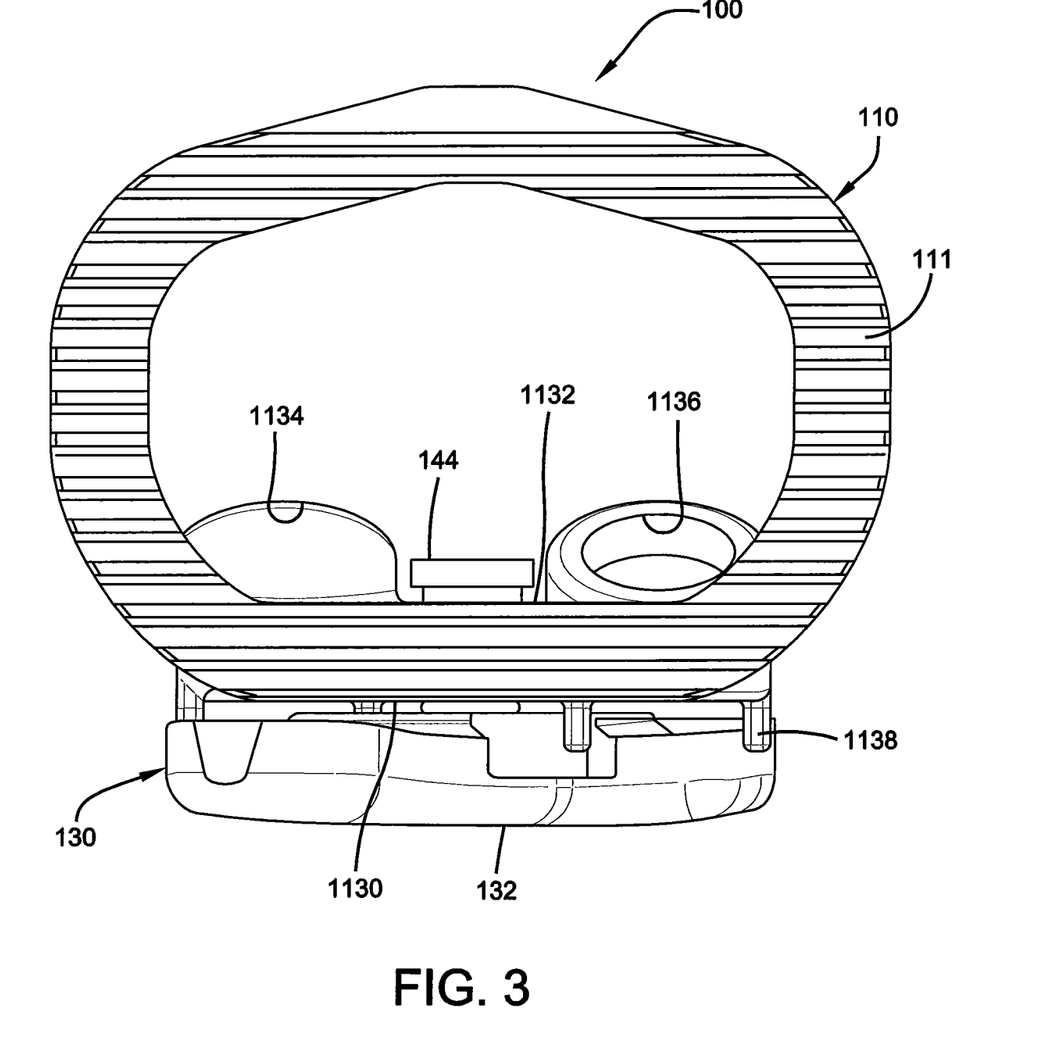
FIG. 3 illustrates a top view of the vertebral implant of FIG. 1 with the plate rotated in accordance with the disclosed architecture.
Figure 4:
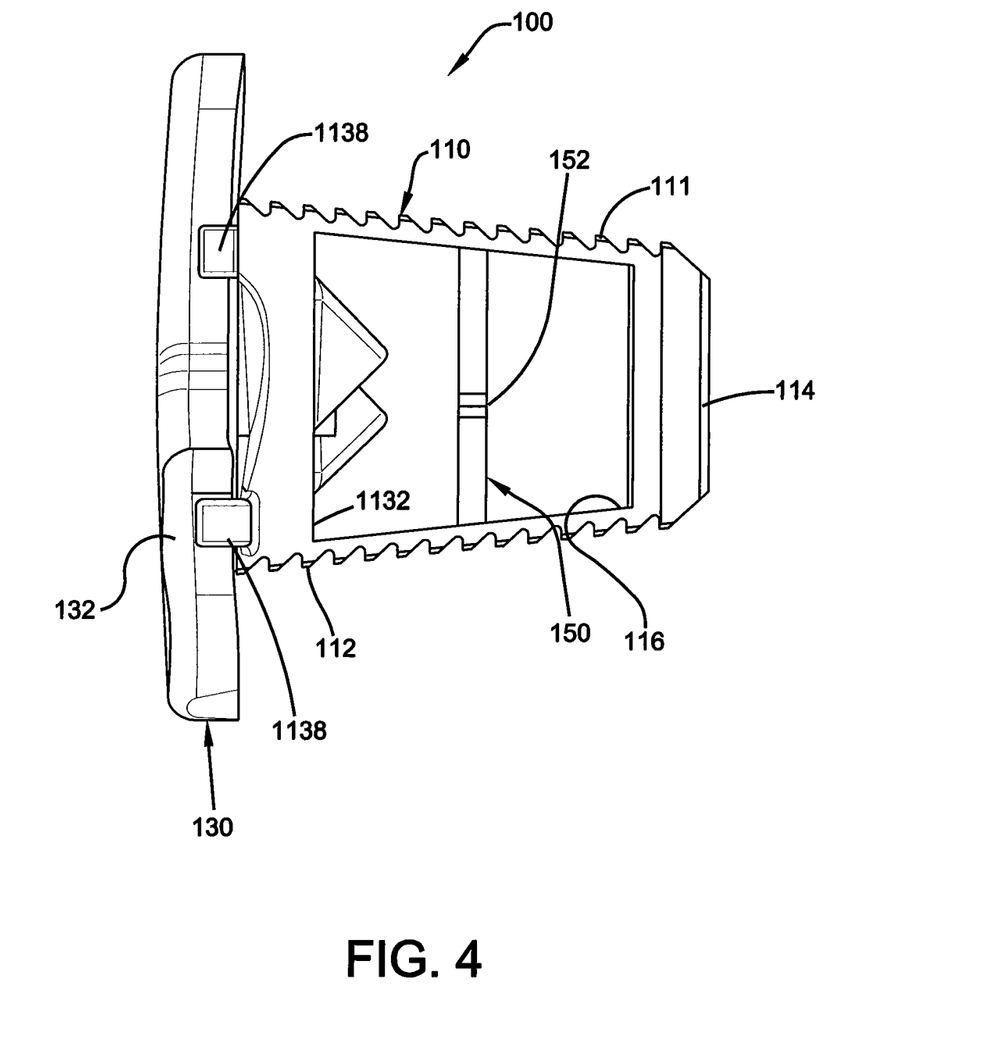
FIG. 4 illustrates a side elevational view of a vertebral implant in accordance with the disclosed architecture.
Figure 5:
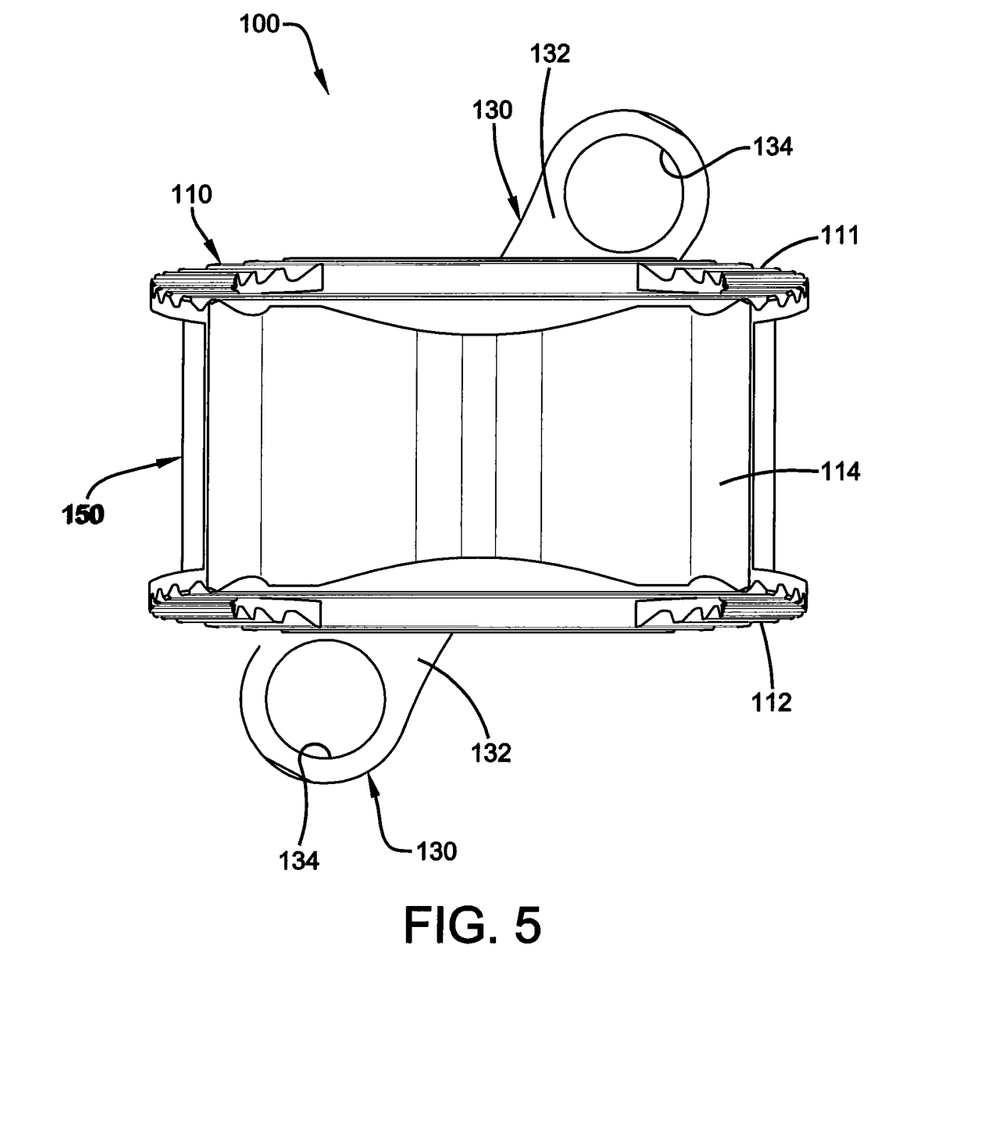
FIG. 5 illustrates a rear elevational view of a vertebral implant in accordance with the disclosed architecture.

Cage 110 is preferably comprised of a top 111, a bottom 112, an anterior portion 113, a posterior portion 114, a lateral continuous opening 116 and a vertical continuous opening 118. As best shown in FIGS. 1-3, the surfaces of each of top 111 and bottom 112 are preferably roughened or ridged so as to better grip the adjacent vertebra once installed in a patient. More specifically, the roughened surfaces of top 111 and bottom 112 provide anti-migration features for implant 100 once inserted into the body, and also provides osteo-integration allowing bone to grow within the roughened surfaces to further secure implant 100 within the body.

Anterior portion 113 may be generally curved in shape as shown in the FIGS. and is further comprised of an outboard face 1130, an inboard face 1132, a first opening 1134, a second opening 1136, and a plurality of protrusions or stops 1138 strategically positioned in spaced apart fashion along the outboard face 1130 for limiting the rotation of plate 130, as described more fully below. As best illustrated in FIGS. 1-3, each of first opening 1134 and second opening 1136 extend between outboard face 1130 and inboard face 1132, and are preferably both angled (relative to outboard face 1130) and threaded for receipt of a surgical screw (not shown) for securing implant 100 to adjacent vertebra. Further, in a preferred embodiment of the present invention, first opening 1134 and second opening 1136 will be angled in different directions to ensure a more secure attachment to the patient. For example, first opening 1134 may be generally angled downward towards bottom 112 (as shown in FIG. 1.), whereas second opening 1136 may be generally angled upward towards top 111 (as also shown in FIG. 1), or vice versa. Of course, one of ordinary skill in the art will appreciate that many other angled configurations/combinations may also be used.

Lateral continuous opening 116 extends between anterior portion 113 and posterior portion 114, and between top 111 and bottom 112. Lateral continuous opening 116 is useful for promoting bone growth in implant 100 following surgical implantation. Similarly, vertical continuous opening 118 extends between top 111 and bottom 112 and intersects with lateral continuous opening 116. Vertical continuous opening 118 is also useful for promoting bone growth in implant 100 following surgical implantation. As best shown in FIG. 1, cage 110 may further comprise webbing 119 for the promotion of osteo-integration and to allow bone to grow within the webbing 119 to further secure implant 100 within the body.

Notwithstanding, one of ordinary skill in the art will appreciate that the shape and size of the cage 110, as shown in FIGS. 1-5, are for illustrative purposes only and that many other shapes and sizes of cage 110 are well within the scope of the present disclosure. Although dimensions of cage 110 (i.e., length, width, and height) are important design parameters for good performance, cage 110 may be any shape or size that ensures optimal performance during use.

As best shown in FIGS. 1-3, plate 130 is comprised of an elongated body portion 132 with a plurality of continuous openings 134 formed therein for receipt of fasteners (not shown) as described more fully below. Plate 130 is rotatably secured to cage 110 by fastener mechanism 140, or may be integrally formed with cage 110 via additive manufacturing techniques, as more fully described below. More specifically, the plate 130 is rotatable about an axis that is substantially perpendicular to the outboard face 1130 of anterior portion 113. Fastener mechanism 140 is preferably comprised of a post 142 and a flange 144, and prevents plate 130 from separating from anterior portion 113 of cage 110. Further, support material 160 may be added during the additive manufacturing process to lend support to implant 100, and is preferably positioned around post 142 of fastener mechanism 140 during the manufacturing of implant 100. More specifically, support material 160 retains plate 130 in place relative to anterior portion 113 as both components are formed. Support material 160 is typically a water-soluble support material, but can be any suitable support structure or material as is known in the art. Once implant 100 is formed, support material 160 may be dissolved away, allowing the plate 130 to rotate about post 142 independently from cage 110, but to still remain movably attached to cage 110 via the flange 144.

Notwithstanding the forgoing, one of ordinary skill in the art will appreciate that the shape and size of plate 130 as shown in FIGS. 1-5 is for illustrative purposes only and many other shapes and sizes of plate 130 are well within the scope of the present disclosure. Although dimensions of plate 130 (i.e., length, width, height, locations of openings 134) are important design parameters for good performance, plate 130 may be any shape or size that ensures optimal performance during use and is within the overall objective of the present invention.

During surgical insertion of implant 100 into a patient between two vertebra (not shown), plate 130 is substantially in a vertical position relative to cage 110 as shown in FIG. 1. Once implant 100 is properly installed in the patient and fasteners (not shown) are inserted into first opening 1134 and second opening 1136 of anterior portion 113 and into the patient's bone, plate 130 may be rotated approximately 30 degrees in a counterclockwise direction to prevent or block said fasteners from "backing out" or otherwise becoming unsecured. After plate 130 has been rotated into said position, implant 100 can be further secured by additional fasteners (not shown) that are inserted through openings 134 in plate 130 and into the patient's bone (not shown). These additional fasteners may be self-tapping and create threads in openings 134 of plate 130. In this manner, implant 100 can be secured to patient with at least four different fasteners, and plate 130 is prevented from further rotating relative to cage 110 and effectively blocks the fasteners inserted through cage 110 from becoming unsecured.

Additionally, during the installation of implant 100 and prior to plate 130 being secured to the patient's bone, over rotation of plate 130 is prevented, and rotation and counter-rotation in general are somewhat limited, by the presence of strategically placed stops 1138 along the outboard face 1130 of anterior portion 113, as best shown in FIGS. 1-2. Notwithstanding, it is also contemplated that stops 1138 may be positioned elsewhere along outboard face 1130 of anterior portion 113 to allow for more or less rotation than the above stated 30 degrees to suit a particular application.

As previously stated, the ALIF implant 100 of the present invention may be integrally manufactured using additive manufacturing techniques, or by using a combination of other molding or machining techniques (injection molding, machining, etc.) to produce the subject encoded implant. These additional techniques include, without limitation, material extrusion, vat photo polymerization, powder bed fusion, material jetting, binder jetting, sheet lamination and directed energy deposition. Typically, implant 100 is manufactured from titanium, specifically Ti 6 Al 4 V-ELI, but implant 100 can be manufactured from any other suitable material as is known in the art.

In a preferred embodiment, cage 110 and plate 130 are manufactured or grown together as one integral component using additive manufacturing techniques. Since the two components are grown together, the plate lengths and cage heights are proportional to each other, and thus there is no need for a range of separate sizes in cages 110 and plates 130 as would typically be required. Cage 130 may also be manufactured with webbing or other honey-combed like structure 119 on its exterior or interior surfaces to promote bone growth within implant 100, and osteo-integration.

As referenced above, implant 100 may further comprise a structurally encoded member 150 having a plurality of notches or other inclusions 152 therein representing encoded data. By way of further example, FIGS. 1, 2, 4 and 5 illustrate a structurally encoded rod 150 that extends from top 111 to bottom 112 on a side of implant 100, and has a plurality of notches 152 therein representing structurally encoded data.

By way of further example, portions of implant 100 such as the surface or interior of cage 110 or plate 130 may also comprise notches 152 or other radiopaque inclusions that interrupt an otherwise uniform surface (or that have a varying density) and that can be encoded with information about the implant 100, its manufacturer, the patient, the facility or physician performing the procedure, etc. in accordance with the inventions disclosed in the incorporated references. The structurally encoded data may also take the form of the rods 150 shown in the FIGS., or the vertical rods 150 can be tantalum rods, that can be coded to match the encoded markers that may be pressed into the implant 100 in accordance with inventions disclosed in the incorporated references. Such encoding may be accomplished for instance through the use of eclipsing patterns of marks or notches in other planes within the cage 110 or plate 130, to reveal a pattern upon elucidation through reading illumination or through illumination-aided visual inspection or optical inspection, as described herein.

The displayed pattern may be used and stored as a unique symbol such as may be done in a fashion similar to bar codes, or other direct correspondence to a file of information such as through pattern recognition. The encoded pattern may further be associated with a database containing a plurality of records associated with a plurality of implantable devices 100 and a user interface comprising means for displaying information associated with the indicia based on the plurality of records. The encoded pattern may in turn be related to a unique numerical identifier corresponding to the associated manufacturer, serial number, installation data, patient, surgeon, or surgical procedure information that may be located in an external healthcare facility or other database.

The structurally encoded member 150 may be read via a system selected from the group consisting of visible light, UV light, x-ray, fluoroscopy, computed tomography, electromagnetic radiation, ultrasound, ultrasound, magnetic resonance imaging, positron emission tomography and neutron imaging. The information or data encoded onto or into the implants of the embodiments disclosed in the present invention may also be detected, decoded, read, transferred, stored, displayed, or processed according to such methods and devices disclosed in U.S. Pat. No. 8,233,967 or U.S. Patent Application Publication No. 2013/0053680, both of which are incorporated herein by reference.

The present invention thus permits the convenient, accurate and efficient reading of structurally encoded articles such as the implant 100 of the present invention. A typical embodiment of the structurally encoded implants 100 of the present invention may contain data that is not readily apparent to a viewer of the device structure. Further, encoding of the typical embodiments of the present invention is handled by physical means other than those accomplished through circuitry, electromagnetic or other, within the implant device itself or through a type of internal storage means such as magnetic storage means or the like. Such structurally encoded devices, as disclosed herein and described in relation to the typical and/or preferred embodiments of the present invention allow simplified production, maintenance, and/or operation costs for identification, storage, and/or retrieval of unique implant data while retaining a substantial amount of information with reduced probability for error.

The implant 100 of the present invention also enables better reporting, reviewing, inventorying and analyzing of implant devices 100 to reduce medical error by enabling healthcare professionals and others to rapidly and precisely identify an implant device 100 and obtain important information concerning the characteristics of the device, principally prior to installation. The present invention enhances analysis of implants on the market by providing a standard and clear way to document device use in electronic health records, clinical information systems, claim data sources, and registries.

It will also be appreciated that the present invention may be applied to similarly prepared articles such as articles that may benefit from structurally encoded structures as in the present invention. Such articles may include parts used in manufacturing, such as in the case of automobiles and parts therefor, firearms and parts therefor or jewelry and parts therefor. The present invention also includes methods of reading the structurally encoded articles, as well as an inventory management system for structurally encoded articles that includes reading the encoded data from the encoded articles and storing the acquired data, as described in the references cited herein.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implant comprising:
a cage comprised of an anterior portion and a posterior portion;
a fastener mechanism;
a plate integrally formed with the cage, wherein the plate is positioned on the anterior portion of the cage;
a water soluble support material that fixes the plate relative to the cage; and
a structurally encoded member.

2. The implant of claim 1, wherein said cage further comprises a top, a bottom, a lateral continuous opening and a vertical continuous opening.

3. The implant of claim 1, wherein the anterior portion further comprises a plurality of stops and at least one opening.

4. The implant of claim 1, wherein the implant is manufactured using additive manufacturing techniques.

5. The implant of claim 1, wherein the implant is manufactured from titanium and further comprises webbing.

6. The implant of claim 1, wherein the water soluble support material is positioned around the fastener mechanism.

7. The implant of claim 6, wherein the water soluble support material holds the plate in place relative to the cage during an implant manufacturing process.

8. An implant comprising:
a cage comprised of an anterior portion and a posterior portion;
a plate integrally formed with the cage;
a fastener mechanism;
a water soluble support material that fixes the plate relative to the cage; and
a structurally encoded member.

9. The implant of claim 8, wherein the anterior portion further comprises a plurality of stops that limit a rotation of the plate relative to the cage.

10. The implant of claim 8, wherein the anterior portion further comprises a threaded opening therein for receipt of a fastener, and further wherein said threaded opening is at a first angle relative to an outboard face of the anterior portion.

11. The implant of claim 10, wherein the anterior portion further comprises a second threaded opening at a second angle relative to the outboard face, and further wherein said second angle is different than the first angle.

12. The implant of claim 8, wherein the structurally encoded member is a rod with a plurality of notches therein.

13. The implant of claim 8, wherein the structurally encoded member is readable by a system selected from the group consisting of visible light, UV light, x-ray, fluoroscopy, computed tomography, electromagnetic radiation, ultrasound, magnetic resonance imaging, positron emission tomography and neutron imaging.

14. An implant comprising:
a cage comprised of a posterior portion and an anterior portion having an outboard face;
a fastener mechanism;
a structurally encoded member; and
a plate with at least one opening therein, wherein said plate is integrally formed with said cage, and further wherein said cage is fixed to said plate by a water soluble support material.

15. The implant of claim 14, wherein the anterior portion comprises at least one continuous opening therein for receipt of the fastener mechanism, and said plate is rotatable about an axis that is substantially perpendicular to the outboard face.

16. The implant of claim 15, wherein said plate is rotatable into a position that prevents the fastener mechanism from being removed from the at least one continuous opening.

17. The implant of claim 14, wherein the fastener mechanism is comprised of a post and a flange.

18. The implant of claim 17 wherein the water soluble support material is positioned adjacent to said fastener mechanism, and further wherein said implant is manufactured using additive manufacturing techniques.

* * * * *